(12) United States Patent
Lim et al.

(10) Patent No.: US 7,147,817 B1
(45) Date of Patent: Dec. 12, 2006

(54) METHOD OF MAKING A LOW PROFILE BALLOON

(75) Inventors: Florencia Lim, Union City, CA (US); Timothy Owens, Dublin, CA (US); Srinivasan Sridharan, Morgan Hill, CA (US); Chi Le Long, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 313 days.

(21) Appl. No.: 10/335,484

(22) Filed: Dec. 31, 2002

(51) Int. Cl.
*B29C 49/22* (2006.01)
*B29C 49/64* (2006.01)

(52) U.S. Cl. .................. 264/289.6; 264/572; 264/573

(58) Field of Classification Search ..... 604/96.01–103, 604/509; 156/84–86, 381–382; 606/191–195; 264/289.6
See application file for complete search history.

(56) References Cited

U.S. PATENT DOCUMENTS

| | | | |
|---|---|---|---|
| 4,251,305 A * | 2/1981 | Becker et al. ............. 156/86 |
| 4,636,272 A * | 1/1987 | Riggs ...................... 156/158 |
| 5,147,302 A * | 9/1992 | Euteneuer et al. ......... 604/103 |
| 5,374,473 A | 12/1994 | Knox et al. |
| 5,788,626 A | 8/1998 | Thompson |
| 5,791,036 A * | 8/1998 | Goodin et al. ............. 29/423 |
| 5,833,657 A * | 11/1998 | Reinhardt et al. ....... 604/101.02 |
| 5,868,704 A | 2/1999 | Campbell et al. |
| 5,964,730 A * | 10/1999 | Williams et al. ............ 604/103 |
| 6,016,848 A * | 1/2000 | Egres, Jr. .................... 138/137 |
| 6,120,477 A | 9/2000 | Campbell et al. |
| 6,139,525 A * | 10/2000 | Davis-Lemessy et al. .. 604/103 |
| 6,428,506 B1 | 8/2002 | Simhambhatla et al. |
| 6,465,067 B1 * | 10/2002 | Wang et al. ............... 428/35.7 |
| 6,863,757 B1 | 3/2005 | Gonzalez et al. |
| 2004/0068287 A1 | 4/2004 | Lim |

FOREIGN PATENT DOCUMENTS

| WO | WO 95/05555 | 2/1995 |
|---|---|---|
| WO | WO 97/02791 | 1/1997 |
| WO | WO 01/45766 A1 | 6/2001 |

* cited by examiner

*Primary Examiner*—Christina Johnson
*Assistant Examiner*—Monica A Huson
(74) *Attorney, Agent, or Firm*—Fulwider Patton LLP (57) ABSTRACT

A method of making a catheter balloon or other expandable tubular medical device or component thereof, in which an assembly of heat shrink material on an outer surface of coaxially disposed first and second tubes is heated to radially shrink the heat shrink material and reduce the outer diameter of the first tube. In a presently preferred embodiment, the heat shrink material extends at least along a central section of the first tube to reduce the outer diameter of the first tube at least along the central section of the first tube. The first and second tubes form the outer and inner layers, respectively, of a multilayered balloon, which has an improved low profile outer diameter.

18 Claims, 3 Drawing Sheets

METHOD OF MAKING A LOW PROFILE BALLOON

BACKGROUND OF THE INVENTION

This invention generally relates to medical devices, and particularly to intracorporeal devices for therapeutic or diagnostic uses such as balloon catheters, and vascular grafts.

In percutaneous transluminal coronary angioplasty (PTCA) procedures, a guiding catheter is advanced until the distal tip of the guiding catheter is seated in the ostium of a desired coronary artery. A guidewire, positioned within an inner lumen of a dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with fluid one or more times to a predetermined size at relatively high pressures (e.g. greater than 8 atmospheres) so that the stenosis is compressed against the arterial wall to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e., reformation of the arterial blockage, which necessitates either another angioplasty procedure or some other method of repairing or strengthening the dilated area. To reduce the restenosis rate and strengthen the dilated area, physicians frequently implant a stent inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to an angioplasty balloon catheter, and expanded to a larger diameter by expansion of the balloon. The balloon is deflated to remove the catheter and the stent left in place within the artery at the site of the dilated lesion. Stent covers commonly provided on an inner or an outer surface of the stent have been used in, for example, the treatment of pseudo-aneurysms and perforated arteries and to prevent prolapse of plaque, and generally comprise a cylindrical tube of synthetic or natural material. Similarly, vascular grafts comprising cylindrical tubes commonly made from tissue or synthetic materials such as polyester, expanded polytetrafluoroethylene, and DACRON, are configured to be implanted in vessels to strengthen or repair the vessel, or used in an anastomosis procedure to connect vessels segments together.

In the design of catheter balloons, characteristics such as strength, compliance, and profile of the balloon are carefully tailored depending on the desired use of the balloon catheter, and the balloon material and manufacturing procedure are chosen to provide the desired balloon characteristics. A variety of polymeric materials are conventionally used in catheter balloons. Use of polymeric materials such as PET that do not stretch appreciably consequently necessitates that the balloon is formed by blow molding, and the deflated balloon material is folded around the catheter shaft in the form of wings, prior to inflation in the patient's body lumen. However, it can be desirable to employ balloons, referred to as formed-in-place balloons, that are not folded prior to inflation, but which instead readily expand to the working diameter within the patient's body lumen from a generally cylindrical or tubular shape (i.e., essentially no wings) that conforms to the catheter shaft.

Catheter balloons formed of expanded polytetrafluoroethylene (ePTFE) expanded in place within the patient's body lumen without blow molding the ePTFE tubing have been disclosed. Prior disclosed methods of forming the ePTFE balloon involve wrapping a sheet of ePTFE on a mandrel and then heating the wrapped sheet to fuse the layers of wrapped material together. However, one difficulty has been further processing the resulting ePTFE tube after the layers of wrapped material are fused together without damaging the ePTFE tube.

SUMMARY OF THE INVENTION

This invention is directed to a method of making a catheter balloon or other expandable tubular medical device or component thereof, in which an assembly of heat shrink material on an outer surface of coaxially disposed first and second tubes is heated to radially shrink the heat shrink material and reduce the outer diameter of the first tube. In a presently preferred embodiment, the heat shrink material extends at least along a central section of the first tube to reduce the outer diameter of the first tube at least along the central section of the first tube. The first and second tubes form the outer and inner layers, respectively, of a multilayered balloon, which has an improved low profile outer diameter.

The method of the invention generally comprises positioning on a distal section of a catheter shaft a first and a second tube, with the first tube on an outer surface of the second tube, and with a proximal end section and a distal end section of at least one of the first and second tubes in contact with the catheter shaft, the first tube forming an outer layer of a multilayer balloon and the second tube forming an inner layer of the multilayer balloon. Heat shrink material is positioned on an outer surface of the first tube (with the first tube already in position on the second tube) to form an assembly, with the heat shrink material extending at least along a central section of the first tube located between the proximal and distal end sections of the first tube. The heat shrink material is radially shrunk by heating the heat shrink material on the first tube, to reduce the outer diameter of the first tube at least along the central section of the first tube. The shrunk heat shrink material is removed from the reduced diameter first tube, to form a balloon catheter having a reduced diameter multilayered balloon. Preferably, the method includes pressurizing an interior of the second tube to radially expand a central section of the second tube during shrinking of the heat shrink material, to prevent an inner surface of the central section of the second tube from becoming adhered to an underlying section of the catheter shaft extending through the inflatable interior of the balloon. As a result, the flow of inflation fluid into the balloon interior is not restricted, unlike in a balloon in which a portion of the central section of the second tube becomes adhered to the underlying section of the shaft. Additionally, the heat shrink material on the first and second tubes reduces heat transfer from outside to the first and second tubes, to further reduce the tendency of the central section of the second (i.e., inner) tube to become adhered to the underlying section of the shaft.

In a first embodiment, the heat shrink material reduces the outer diameter of the first and second tubes during the bonding together of the first and second tubes (e.g., during lamination of the balloon layers). Thus, the assembly of the heat shrink material on the first and second tubes, before radially shrinking the heat shrink material, has at least a section of the first tube in contact with but not yet bonded to the second tube. In a presently preferred embodiment, the assembly is placed in an interior chamber of a balloon press before heating the heat shrink material, and the assembly is heated as the first and second tubes are pressed together in the balloon press, to bond an inner surface of the first tube to an outer surface of the second tube. The heat shrink material preferably radially compresses the first tube, so that the shrunk assembly has an outer diameter which is less than a diameter of the interior chamber of the balloon press. Consequently, in one embodiment, the central section of the first tube has a reduced outer diameter, after the heat shrink material is radially shrunk during lamination of the first and second tubes, which is at least about 10% less than, and more specifically about 10% to about 20% less than, the diameter of the interior chamber of the balloon press in which the layers are laminated together.

In another embodiment, the first and second tubes are already bonded together and to the shaft before the heat shrink tubing is positioned thereon. Thus, the assembly of the first and second tubes forming the inner and outer layers of the balloon with the heat shrink material thereon (before radially shrinking the heat shrink material) has at least a section of the first tube, and typically a significant portion of the length thereof, bonded to the second tube. In one embodiment, heating the assembly to radially shrink the heat shrink material reduces the outer diameter of the balloon central section by at least about 4%, more specifically about 4% to about 8%. In a presently preferred embodiment, the bonded first and second tubes were bonded together as discussed above in relation to the first embodiment with heat shrink material on the tubes in the balloon press. Thus, in a presently preferred embodiment, two separate assemblies of heat shrink material are used during formation of the balloon catheter, namely, the first heat shrink member used to reduce the outer diameter of the first tube on the second tube during bonding together of the first and second tubes, and the second heat shrink member used thereafter to further reduce the outer diameter of the multilayer balloon attached to the catheter shaft.

In a presently preferred embodiment, the first tube is a porous polymeric material selected from the group consisting of expanded polytetrafluoroethylene (ePTFE), an ultra high molecular weight polyolefin including ultra high molecular weight polyethylene, porous polyolefins including polyethylene and polypropylene, and porous polyurethane. In one embodiment, the porous material has a node and fibril microstructure. ePTFE and ultra high molecular weight polyethylene (also referred to as "expanded ultra high molecular weight polyethylene") typically have a node and fibril microstructure, and are not melt extrudable. The node and fibril microstructure, when present, is produced in the porous material using conventional methods, and the tube of porous polymeric material preferably has the desired microstructure (e.g., porous and/or node and fibril) before the heat shrink material is positioned thereon. However, a variety of suitable polymeric materials can be used in the method of the invention including conventional catheter balloon materials which are melt extrudable. In one presently preferred embodiment, the porous polymeric material forming the first tube cannot be formed into a balloon by conventional balloon blow molding, and is formed into a balloon by bonding a sheet of the porous polymeric material together to form a tubular member, and preferably provided with a nonporous second layer or liner (i.e., the second tube) to form an inflatable balloon. The porous polymeric tube is typically formed by wrapping a sheet of porous polymeric material on a mandrel and heating the wrapped sheet to fuse sections of the sheet together.

In a presently preferred embodiment, the heat shrink material comprises a tube of heat shrink material with an inner diameter configured to slidably receive the coaxial first and second tubes therein. In another embodiment, the heat shrink material positioned on the first and second tubes comprises a sheet of heat shrink material wrapped around the porous polymeric tube at least one time, and typically multiple times.

In a presently preferred embodiment, the heat shrink material is conventional commercially available heat shrink tubing, selected from the group consisting of low density polyethylene, and polypropylene and polytetrafluoroethylene or the copolymers thereof. The heat shrink material is preferably radially oriented material, which thus has radial shrinkage during heat shrinking thereof. A variety of suitable commercially available oriented heat shrink material may be used including low density polyethylene (LDPE).

The heat shrink material shrinks radially to reduce the outer diameter of the assembly of the first tube on the second tube, typically by both radially compacting the porous material of the first tube, and by reducing the inner and outer diameters of the first and second tubes (i.e., independent of any reduction in wall thickness). The porous material of the first tube is somewhat compressible due to the porosity of the material. However, the porous material of the first tube is typically compacted prior to bonding to the second tube, so that the porous material is typically not in a highly compressible state during the shrinking of the heat shrink material thereon.

Preferably, the heat shrink material shrinks radially to a substantially greater degree than axially. The resulting decrease in the outer diameter produced in the first tube is expressed herein as a percentage diameter reduction. Thus, an assembly of a first tube on a second tube (i.e., an ePTFE tube on an outer surface of the second tube) having an original outer diameter (i.e., the outer diameter of the first tube just prior to heating the heat shrink material) of 0.046 cm, which is subsequently reduced to a diameter of 0.043 cm, has a reduced outer diameter which is about 6.5% less than the original outer diameter.

A balloon formed according to the method of the invention can be used on a variety of suitable balloon catheters including coronary and peripheral dilatation catheters, stent delivery catheters, drug delivery catheters and the like. Although discussed below primarily in terms of the embodiment in which the medical device tubular component is an inflatable member such as a balloon for a catheter, it should be understood that other expandable medical devices and components are included within the scope of the invention including stent covers and vascular grafts.

The method of the invention provides an improved low profile catheter balloon with a balloon having a reduced outer diameter at least along a central section thereof. Moreover, the method allows for reducing the outer diameter of the balloon while preventing or limiting the inner surface of the balloon from becoming adhered to the underlying section of the catheter shaft. These and other advantages of the invention will become more apparent from the following detailed description and accompanying exemplary figures.

DETAILED DESCRIPTION OF THE INVENTION

Figures 1, 2, 3:
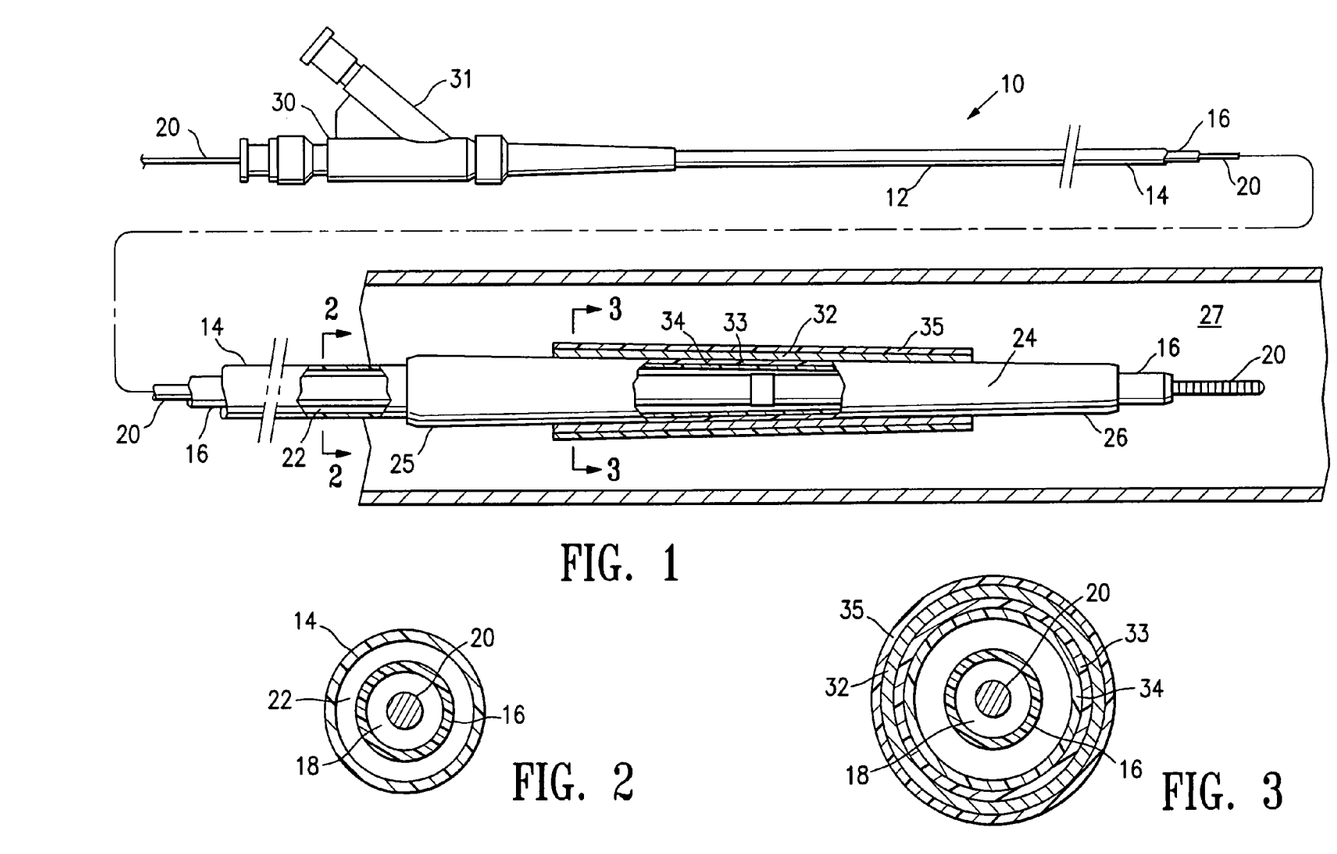
FIG. 1 is an elevational view, partially in section, of a balloon catheter having a balloon with an inner layer and an outer layer, formed according to a method which embodies features of the invention.
FIGS. 2 and 3 illustrate transverse cross sections of the balloon catheter of FIG. 1, taken along lines 2—2 and 3—3, respectively.
Figure 4:
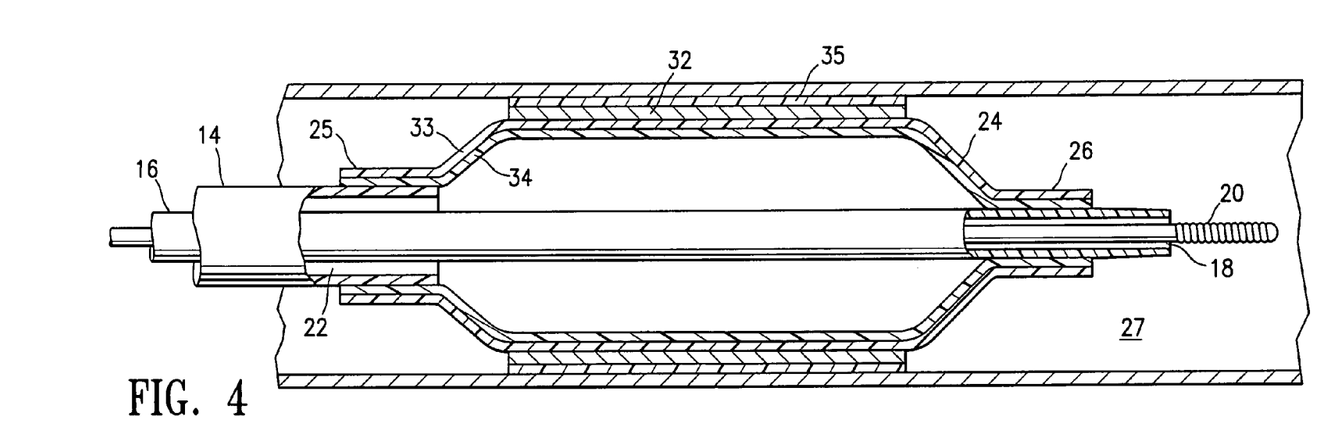
FIG. 4 illustrates the balloon catheter of FIG. 1, with the balloon fully inflated in the patient's body lumen.

FIG. 1 illustrates an over-the-wire type stent delivery balloon catheter 10 embodying features of the invention. Catheter 10 generally comprises an elongated catheter shaft 12 having an outer tubular member 14 and an inner tubular member 16. Inner tubular member 16 defines a guidewire lumen 18 configured to slidingly receive a guidewire 20, and the coaxial relationship between outer tubular member 14 and inner tubular member 16 defines annular inflation lumen 22, as best shown in FIG. 2 illustrating a transverse cross section view of the distal end of the catheter shown in FIG. 1, taken along line 2—2. An inflatable balloon 24 disposed on a distal section of catheter shaft 12 has a proximal skirt section 25 sealingly secured to the distal end of outer tubular member 14, a distal skirt section 26 sealingly secured to the distal end of inner tubular member 16, and an inflatable central section between the proximal and distal skirt sections, so that its interior is in fluid communication with inflation lumen 22. An adapter 30 at the proximal end of catheter shaft 12 is configured to provide access to guidewire lumen 18, and to direct inflation fluid through arm 31 into inflation lumen 22. In the embodiment illustrated in FIG. 1, the balloon 24 is shown prior to being fully inflated in a patient's body lumen 27, with a stent 32 having a cover 35 mounted on a central working length of the balloon 24. The distal end of catheter may be advanced to a desired region of a patient's body lumen 27 in a conventional manner and balloon 24 inflated to expand the covered stent 32. FIG. 4 illustrates the balloon fully inflated in the body lumen 27.

In the embodiment illustrated in FIG. 1, balloon 24 has a first layer 33 and a second layer 34. In a presently preferred embodiment, the balloon 24 has at least one layer comprising a porous polymeric material, and preferably a microporous polymeric material having a node and fibril microstructure, such as ePTFE. In the embodiment illustrated in FIG. 1, first layer 33 is formed of ePTFE, and the second layer 34 is formed of a polymeric material preferably different from the polymeric material of the first layer 33. Although discussed below in terms of one embodiment in which the first layer 33 is formed of ePTFE, it should be understood that the first layer may comprise other materials including ultrahigh molecular weight polyethylene. The second layer 34 is preferably formed of an elastomeric material, including polyurethane elastomers, silicone rubbers, styrene-butadiene-styrene block copolymers, polyamide block copolymers, and the like. In a preferred embodiment, layer 34 is an inner layer relative to layer 33, although in other embodiments it may alternatively be an outer layer of the balloon 24. Layer 34 formed of an elastomeric material limits or prevents leakage of inflation fluid through the microporous ePTFE to allow for inflation of the balloon 24, and expands elastically to facilitate deflation of the balloon 24 to a low profile deflated configuration. The elastomeric material forming layer 34 may consist of a separate layer which neither fills the pores nor disturbs the node and fibril structure of the ePTFE layer 33, or it may at least partially fill the pores of the ePTFE layer. The layers 33 and 34 each have a length extending from the proximal skirt section 25 to the distal skirt section 26. In the embodiment of FIG. 1, the layers 33 and 34 have about equal lengths, so that the proximal and distal skirt sections 25, 26 are formed by the end sections of the outer layer 33 bonded to the end sections of the inner layer 34 which are bonded to the shaft. In an alternative embodiment (not shown), one or both ends of the outer layer 33 may extend beyond the ends of the inner layer 34 and onto the shaft, so that the proximal and/or distal skirt sections 25, 26 are also formed by end sections of the outer layer 33 bonded directly to the shaft 12.

The balloon catheter 10 is formed according to a method which embodies features of the invention, in which heat shrink material on an outer surface of balloon outer layer 33 is heated to radially shrink the heat shrink material, to reduce the profile of the balloon 24.

Figure 5:
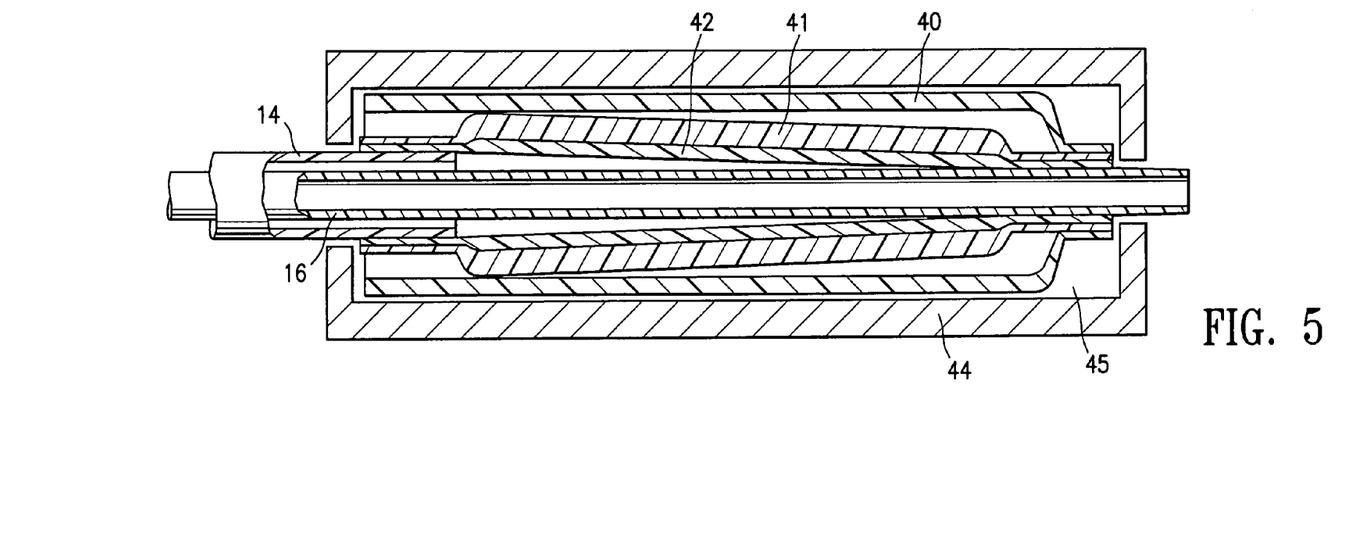
FIG. 5 is a longitudinal cross sectional view of an assembly of heat shrink material on a porous polymeric first tube on a second tube in a balloon press, for laminating the first and second tubes together, during assembly of the balloon catheter of FIG. 1 in a method embodying features of the invention.

FIG. 5 illustrates an assembly of heat shrink material 40 on an outer surface of a first tube 41 which is on an outer surface of a second tube 42, with the assembly in position in a balloon press 44 for bonding the first tube 41 to the second tube 42. The first and second tubes 41, 42 form the balloon outer and inner layers 33, 34, respectively. The tubes 41, 42 typically have an adhesive therebetween or are otherwise treated as for example with a functionalizing surface treatment, so that the tubes 41, 42 will bond together under heat and pressure. Preferably, the proximal and distal skirt sections 25, 26 have been formed by bonding the ends of the first tube 41 and the second tube 42 together and to the shaft 12 (i.e., to the outer tubular member 14 and the inner tubular member 16) before heat shrink material 40 is placed therearound. However, in one embodiment, the proximal and distal ends of the second tube 42 are bonded to the shaft 12, and the proximal and distal ends of the first tube 41 are placed in contact with the second tube 42 or with the shaft 12 but not necessarily bonded thereto before the heat shrink material 40 is placed therearound. In the embodiment in which the first tube 41 is formed of ePTFE, to provide the desired properties such as the desired dimension, and dimensional stability (e.g., to minimize changes in length occurring during inflation of the balloon 24), the first tube 41 is typically stretched, sintered, compacted, and then sintered again prior to being positioned on the second tube 42 for bonding thereto.

In the embodiment of FIG. 5, the heat shrink material 40 is a tube with a lumen configured to be slid over the first tube 41. The heat shrink tubing 40 has a length preferably equal to or greater than the entire length of the first and second tubes 41, 42. In alternative embodiments (not shown), the heat shrink tubing 40 length is less than the length of the first and second tubes 41, 42, and preferably is at least sufficiently long to cover the inflatable central section of the first tube 41. In a presently preferred embodiment, the heat shrink tubing 40 is formed of low density polyethylene (LDPE) heat shrink material which has been placed on a pin gauge or mandrel and heated in a hot box set at about 270° C., to preliminarily shrink the heat shrink tubing along its entire length onto the pin gauge or mandrel. FIG. 5 illustrates the preliminarily shrunk heat shrink tubing 40, after being removed from the pin gauge or mandrel, trimmed in length, and positioned on the first tube 41. With the heat shrink tubing 40 thus on the first tube 41, the distal end of the heat shrink tubing 40 is heated (preferably at about 270° C. for LDPE) to shrink the distal end of the heat shrink tubing 40 tightly onto the outer surface of the first tube 41, and the resulting assembly of heat shrink tubing 40 on first tube 41 on second tube 42 is placed in the interior chamber 45 of balloon press 44, as illustrated in FIG. 5. Although not illustrated, a mandrel may be provided in the inner lumen of the inner tubular member 16 during the bonding of the first and second tubes 41, 42.

In the embodiment of FIG. 5, the balloon press 44 generally comprises a mold. The wall defining the interior chamber 45 preferably collapses to reduce the diameter of the interior chamber 45 from an original diameter to a collapsed diameter. For example, in one embodiment, the balloon press is a collet-like structure with wall sections which move together to reduce the diameter of the interior chamber 45. The original diameter of the interior chamber 45 depends on the outer diameter of the assembly and is preferably sized so that the assembly is tightly fit therein.

Figures 6, 7, 9:
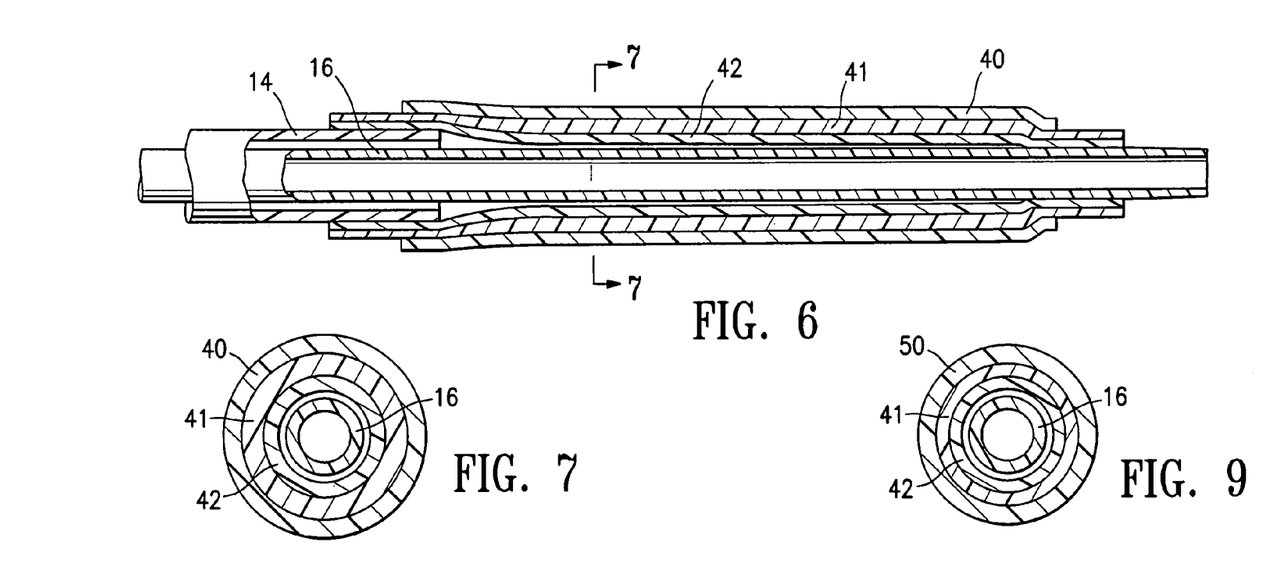
FIG. 6 illustrates the assembly of FIG. 5 after the heat shrink material is heated and the first and second tubes are pressed together and removed from the balloon press, to form the balloon catheter of FIG. 1 having a multilayered balloon on a catheter shaft.
FIG. 7 is a transverse cross sectional view of the assembly shown in FIG. 6, taken along line 7—7.
FIG. 9 is a transverse cross sectional view of the assembly shown in FIG. 8, taken along line 9—9.

The assembly is placed in the balloon press 44 and the collet-like mechanism of the balloon press 44 is closed to decrease the diameter of the interior chamber 45. With the assembly in the heated balloon press 44 as illustrated in FIG. 5, the interior of the second tube 42 is pressurized with air to about 20 psi, and the heat shrink tubing 40 on the first and second tubes presses against an inner surface of the balloon press. However, at the same time, the heat from the balloon press causes the heat shrink tubing 40 to radially shrink. Thus the pressurized air applies a radially outward force, and the heat shrink tubing 40 applies a radially inward force, with the forces combining to press and bond the first and second tubes together and form a shrunk assembly. The heating/pressing typically lasts about 10 to about 60 seconds, preferably about 10 to about 30 seconds, with the balloon press set temperature of about 200 to about 300 degrees Fahrenheit. FIG. 6 illustrates the resulting shrunk assembly after being removed from the balloon press 44.

Without the radially inward force of the heat shrink tubing 40 on the outer surface of the first tube 41, the assembly would be merely pressed against the inner surface of the balloon press of the mold. However, the heat shrink tubing 40 radially shrinks, typically decreasing the diameter of the assembly. In one embodiment, a decrease in the outer diameter of the first tube 41 as the heat shrink tubing shrinks is counteracted by a simultaneous longitudinal shrinkage of the first tube 41, although the inner diameter of the assembly is decreased due to the radially inward force of the shrink tubing. The pressurized air in the second tube 42 keeps the inner surface of the central section of the second tube 42 from being pressed down onto and adhering to the underlying section of the inner tubular member 16 of the catheter shaft. However, the radially inward force of the shrinking heat shrink tubing 40 works against the radially expansive force of the pressurized air, so that the tubes 41, 42 are tightly pressed together, and the resulting bonded tubes 41, 42 have a low profile diameter. In one embodiment, the central section of the first tube 41 (with the first tube 41 on the second tube 42) has an original outer diameter of about 0.045 to about 0.056 inches, more specifically about 0.045 to about 0.048 inches before being placed in the balloon press, and has a reduced outer diameter of about 0.038 to about 0.05 inches, more specifically about 0.042 to about 0.046 inches after being bonded to the second tube 42 in the balloon press, for a finished balloon having an expanded working diameter of about 0.08 to about 0.2 inches (about 2 to about 5 mm) and a total length of about 0.3 to about 1.2 inches (about 8 to about 30 mm). In one embodiment, the diameter of the interior chamber 45 of the balloon press 44 is about 0.048 to about 0.052 inches during bonding of the first and second tubes 41, 42, so that without the heat shrink tubing 40 thereon, the resulting first tube 41 bonded to the outer surface of the second tube 42 would have an outer diameter about equal to the diameter of the interior chamber 45. For example, an assembly of heat shrink tubing on a first tube coaxially disposed on a second tube, in a balloon press having an interior chamber with a diameter of about 0.048 to about 0.052 inches, with the first tube having an outer diameter of about 0.046 inches before lamination to the second tube, resulted in the first tube having a reduced outer diameter of about 0.043 inches after lamination to the second tube.

With the shrunk assembly removed from the balloon press 44 as illustrated in FIG. 6, the shrunk heat shrink tubing 40 is removed from the outer surface of the reduced diameter first tube 41, to form balloon catheter 10 having a reduced diameter multilayered balloon 24.

Figure 8:
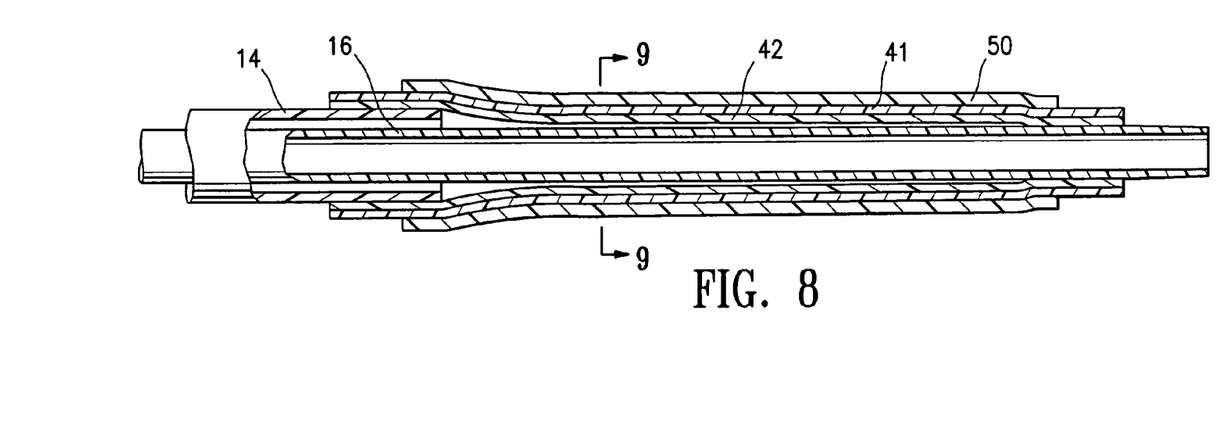
FIG. 8 illustrates a longitudinal cross sectional view of an assembly of heat shrink material placed on a balloon after the balloon first and second layers have been laminated together, after the heat shrink material is heated to reduced the outer diameter of the balloon, in method embodying features of the invention.

In one embodiment, the outer diameter of the multilayered balloon 24 is reduced after the balloon inner and outer layers 33, 34 are bonded together. FIG. 8 illustrates an assembly of heat shrink material 50 on balloon 24, the balloon comprising first tube 41 (forming outer layer 33 in the embodiment of FIG. 1) which is bonded to an outer surface of second tube 42 (forming inner layer 34 in the embodiment of FIG. 1). FIG. 9 illustrates a transverse cross section of FIG. 8, taken along lines 9—9. In the embodiment of FIG. 8, the heat shrink material 50 is a tube with a lumen configured to be slid over the first tube 41. The discussion above relating to the first heat shrink tubing 40 applies to the heat shrink tubing 50. FIG. 8 illustrates the heat shrink tube 50 after the tube 50 has been heated to radially shrink the tube 50 to further reduce the diameter of the balloon 24. Specifically, with the heat shrink tubing extending along at least the central inflatable section of first tube 41, and preferably over the entire length of the first tube 41, the heat shrink tubing is heated and the interior of the balloon 24 is preferably pressurized during shrinking of the heat shrink tube 50, to keep the inner surface second tube 42 (i.e., the balloon inner layer 34) from being pressed down onto the underlying section of the inner tubular member 16 of the catheter shaft. Although not illustrated, a mandrel may be provided in the inner lumen of the inner tubular member 16 during the heat shrinking of heat shrink tube 50 on the first and second tubes 41, 42. The shrunk heat shrink tube 50 is removed from the outer surface of the reduced diameter first tube 41, to form balloon catheter 10 having a reduced diameter multilayered balloon 24.

In one embodiment, the outer diameter of the balloon central section before the heat shrink tubing 50 is radially shrunk thereon is about 0.038 to about 0.056 inches, more specifically about 0.046 to about 0.05 inches, and the reduced outer diameter of the balloon central section is about 0.036 to about 0.048 inches, more specifically about 0.040 to about 0.044 inches after the heat shrink tubing 50 is radially shrunk thereon, for a finished balloon having an expanded working diameter of about 0.08 to about 0.2 inches (about 2 to about 5 mm) and a total length of about 0.3 to about 1.2 inches (about 8 to about 30 mm). Although not illustrated in the embodiment of FIG. 8, in one embodiment, a balloon press similar to balloon press 44 may be used during the heat shrinking of heat shrink tube 50, as discuss above in relation to the embodiment of FIG. 5.

The dimensions of catheter 10 are determined largely by the size of the balloon and guidewires to be employed, catheter type, and the size of the artery or other body lumen through which the catheter must pass or the size of the stent being delivered. Typically, the outer tubular member 14 has an outer diameter of about 0.025 to about 0.04 inch (0.064 to 0.10 cm), more specifically about 0.037 inch (0.094 cm), and a wall thickness of about 0.002 to about 0.008 inch (0.0051 to 0.02 cm), more specifically about 0.003 to 0.005 inch (0.0076 to 0.013 cm). The inner tubular member 16 typically has an inner diameter of about 0.01 to about 0.018 inch (0.025 to 0.046 cm), more specifically about 0.015 to about 0.016 inch (0.038 to 0.04 cm), and a wall thickness of 0.002 to 0.005 inch (0.005 to 0.013 cm). The overall working length of the catheter 10 may range from about 100 to about 150 cm, and is typically about 143 cm. The balloon 24 typically has a length of about 0.5 cm to about 6 cm, and an inflated working diameter of about 2 to about 10 mm.

Although the shaft is illustrated as having an inner and outer tubular member, a variety of suitable shaft configurations may be used including a dual lumen extruded shaft having a side-by-side lumens extruded therein. Similarly, although the embodiment illustrated in FIG. 1 is an over-the-wire stent delivery catheter, the catheter may comprise other types of intravascular catheters, such as rapid exchange dilatation catheters. Rapid exchange catheters generally comprise a distal guidewire port in a distal end of the catheter, a proximal guidewire port in a distal shaft section distal of the proximal end of the shaft and typically spaced a substantial distance from the proximal end of the catheter, and a short guidewire lumen extending between the proximal and distal guidewire ports in the distal section of the catheter.

While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. A method of making a balloon catheter having a multilayer balloon with a proximal skirt section and a distal skirt section bonded to the shaft so that the balloon has an inflatable section with a length between the proximal and distal skirt sections, comprising:

a) providing on a distal section of a catheter shaft a first and a second tube, with the first tube on an outer surface of the second tube, and with a proximal end section and a distal end section of the second tube bonded to the catheter shaft to form at least part of the proximal and distal skirt sections of the balloon, the first and second tubes each extending along the length of the inflatable section from the proximal skirt section to the distal skirt section of the balloon so that the first tube forms an outer layer of the multilayer balloon and the second tube forms an inner layer of the multilayer balloon, and the multilayer balloon has a noninflated configuration with essentially no wings;

b) positioning heat shrink material on an outer surface of the first tube on the second tube to form an assembly, with the heat shrink material extending at least along a central inflatable section of the first tube, said first tube central inflatable section extending the entire length of the first tube located between the proximal and distal end sections of the second tube;

c) pressurizing an interior of the second tube and radially shrinking the heat shrink material by heating the heat shrink material on the first tube, so that the pressurization applies a radially outward force and the heat shrink material applies a radially inward force, to reduce a diameter of the first tube at least along the central inflatable section of the first tube and form a shrunk assembly having the outer surface of the second tube bonded to the first tube along an inflatable length thereof; and d) removing the shrunk heat shrink material from the reduced diameter first tube, to form a balloon catheter having a reduced diameter multilayered balloon with essentially no wings.

2. The method of claim 1 wherein c) includes placing the assembly in an interior chamber of a balloon press before heating the heat shrink material, and c) comprises heating the assembly and pressing the first and second tubes together in the balloon press to bond the first tube to the second tube.

3. The method of claim 2 wherein the first and second tubes are pressed together by reducing the diameter of the interior chamber of the balloon press.

4. The method of claim 3 wherein pressing the first and second tubes together further comprises expanding the assembly against a wall defining the interior chamber of the balloon press.

5. The method of claim 4 wherein the heat shrink tube radially compresses the first tube, so that the shrunk assembly has an outer diameter which is less than a diameter of the interior chamber of the balloon press.

6. The method of claim 5 wherein the central inflatable section of the first tube has a reduced outer diameter after c) which is about 10% to about 20% less than the diameter of the interior chamber of the balloon press.

7. The method of claim 5 wherein the outer diameter of the first tube central inflatable section before c) is about 0.045 to about 0.056 inches, and the reduced outer diameter of the first tube after c) is about 0.042 to about 0.046 inches.

8. The method of claim 2 wherein the second tube is bonded to the shaft before the first tube is placed on the outer surface of the second tube, and the first tube has proximal and distal end sections which are at least in contact with the shaft before being placed in the interior chamber of the balloon press.

9. The method of claim 2 including removing the shrunk assembly from the balloon press before d).

10. The method of claim 2 including after d), positioning heat shrink material on a central section of the reduced diameter multilayered balloon, and shrinking the heat shrink material outer diameter by heating the heat shrink material on the balloon, to further reduce an outer diameter of the balloon at least along the central section of the balloon.

11. The method of claim 1 wherein the first tube is bonded to the second tube before c), and c) comprises heating the assembly to reduce the outer diameter of the balloon central section by about 4% to about 8%.

12. The method of claim 11 wherein the outer diameter of the balloon central section before c) is about 0.038 to about 0.056 inches, and the reduced outer diameter of the balloon central section is about 0.040 to about 0.044 inches after c).

13. The method of claim 12 wherein the first and second tubes are bonded together by heating the first and second tubes in a balloon press with heat shrink material on the first tube so that the heat shrink material radially compresses the first tube in the balloon press.

14. The method of claim 11 and the first and second tubes are bonded together by heating and expanding the first and second tubes in a balloon press with a polytetrafluoroethylene sheath on the first tube, so that the first and second tubes with the sheath thereon expand against a wall defining the interior chamber of the balloon press.

15. The method of claim 14 wherein the outer diameter of the balloon central section after the first and second tubes are heated and expanded in the balloon press but before c) is about 0.048 to about 0.053 inches, and the reduced outer diameter of the balloon central section after c) is about 0.04 to about 0.046 inches.

16. The method of claim 1 wherein the first tube is formed of a porous polymeric material selected from the group consisting of expanded polytetrafluoroethylene, ultra high molecular weight polyolefin, ultra high molecular weight polyethylene, porous polyolefins, porous polyethylene, porous polypropylene, and porous polyurethane, and the second tube is formed of an elastomeric polymeric material, and c) includes pressurizing an interior of the second tube to radially expand a central section of the second tube to prevent an inner surface of the central section of the second tube from bonding to an underlying section of the catheter shaft.

17. The method of claim 1 wherein the heat shrink material is low density polyethylene, and heating the heat shrink material comprises heating the heat shrink material to about 200 to about 300° F.

18. The method of claim 1 wherein the heat shrink material is a tube of cross-linked polymeric material, and heating the heat shrink material comprises heating the heat shrink material to about 200 to about 290° F.

* * * * *

UNITED STATES PATENT AND TRADEMARK OFFICE
CERTIFICATE OF CORRECTION

PATENT NO. : 7,147,817 B1
APPLICATION NO. : 10/335484
DATED : December 12, 2006
INVENTOR(S) : Florencia Lim et al.

It is certified that error appears in the above-identified patent and that said Letters Patent is hereby corrected as shown below:

Column 5,
Line 33, delete "reduced" and insert --reduce--.
Line 34, delete "in method" and insert --in a method--.

Column 9,
Line 22, delete "discuss" and insert --discussed--.

Column 11,
Line 25, delete "claim 11 and" and insert --claim 11 wherein--.

Signed and Sealed this

Twenty-seventh Day of March, 2007

JON W. DUDAS
*Director of the United States Patent and Trademark Office*